(12) United States Patent
Erickson et al.

(10) Patent No.: US 9,001,322 B2
(45) Date of Patent: Apr. 7, 2015

(54) SURFACE ENHANCED RAMAN SCATTERING (SERS) APPARATUS, METHODS AND APPLICATIONS

(75) Inventors: David Erickson, Ithaca, NY (US); Aram J. Chung, Los Angeles, CA (US); Yun Suk Huh, Daejeon (KR)

(73) Assignee: Cornell University, Ithaca, NY (US)

(*) Notice: Subject to any disclaimer, the term of this patent is extended or adjusted under 35 U.S.C. 154(b) by 161 days.

(21) Appl. No.: 13/597,688

(22) Filed: Aug. 29, 2012

(65) Prior Publication Data

US 2013/0050695 A1 Feb. 28, 2013

Related U.S. Application Data

(60) Provisional application No. 61/528,820, filed on Aug. 30, 2011.

(51) Int. Cl.
*G01J 3/44* (2006.01)
*B82Y 30/00* (2011.01)
*B82Y 40/00* (2011.01)
*G01N 21/65* (2006.01)

(52) U.S. Cl.
CPC .............. *B82Y 30/00* (2013.01); *B82Y 40/00* (2013.01); *G01N 21/658* (2013.01)

(58) Field of Classification Search
USPC ......................................................... 356/301
See application file for complete search history.

(56) References Cited

U.S. PATENT DOCUMENTS

| | | | |
|---|---|---|---|
| 5,362,575 A | 11/1994 | Trimble | |
| 6,190,737 B1 * | 2/2001 | Roche et al. | 427/386 |
| 7,658,991 B2 | 2/2010 | Zhao et al. | |
| 7,888,129 B2 | 2/2011 | Hulteen et al. | |
| 7,998,539 B2 | 8/2011 | Chang et al. | |
| 2007/0144345 A1 * | 6/2007 | Borisenko | 95/65 |
| 2009/0257056 A1 | 10/2009 | Demirel et al. | |
| 2009/0263595 A1 | 10/2009 | Ellrich et al. | |
| 2009/0303461 A1 * | 12/2009 | Sun et al. | 356/36 |
| 2010/0042002 A1 * | 2/2010 | Hart et al. | 600/476 |
| 2010/0093171 A1 * | 4/2010 | Zhang et al. | 438/689 |
| 2010/0129623 A1 * | 5/2010 | Johansson et al. | 428/206 |
| 2010/0178568 A1 * | 7/2010 | Unalan et al. | 429/317 |

(Continued)

OTHER PUBLICATIONS

Lei et al.; Surface patterning using templates: concept, properties and device applications; Chem. Soc. Rev., 2011, 40, 1247-1258; The Royal Society of Chemistry 2011.

(Continued)

*Primary Examiner* — Roy M Punnoose
*Assistant Examiner* — Omar Nixon
(74) *Attorney, Agent, or Firm* — William Greener; Bond, Schoeneck & King, PLLC (57) ABSTRACT

Surface enhanced Raman scattering (SERS) substrates may be fabricated using a shadow mask assisted evaporation (SMAE) method to provide for enhanced detection sensitivity with respect to target molecules that are located upon, and sensitized by, the SERS enhanced substrates. Such SERS substrates provide a two dimensional array of repeating nanostructures that may include, but are not limited to nano-pillar, nano-nib, nano-elliptical cylinder and nano-triangular tip nanostructures, any of which may be augmented with gold nanospheres. The particular SERS enhanced substrates in accordance with the embodiments, in particular when augmented with gold nanospheres, provide desirably enhanced sensitivity.

28 Claims, 6 Drawing Sheets

(56) References Cited

U.S. PATENT DOCUMENTS

2010/0197073 A1* 8/2010 Parsons .......................... 438/82
2011/0037976 A1 2/2011 Zhao et al.

OTHER PUBLICATIONS

Boltasseva, Alexandra; Plasmonic components fabrication via nanoimprint; Birck and NCN Publications; Paper 495; http://docs.lib.purdue.edu/nanopub/495.

Chaney et al.; Aligned silver nanorod arrays produce high sensitivity surface-enhanced Raman spectroscopy substrates; Applied Physics Letters 87, 031908 2005; American Institute of Physics.

Driskell et al.; The Use of Aligned Silver Nanorod Arrays Prepared by Oblique Angle Deposition as Surface Enhanced Raman Scattering Substrates; J. Phys. Chem. C 2008, 112, 895-901; American Chemical Society.

Kosiorek et al.; Fabrication of Nanoscale Rings, Dots, and Rods by Combining Shadow Nanosphere Lithography and Annealed Polystyrene Nanosphere Masks; small 2005, 1, No. 4, 439-444; DOI: 10.1002/smll.200400099.

Murphy et al.; Tunable Optical Properties of Metallic Nanotubes; 3rd International Congress on Advanced Electromagnetic Materials in Microwaves and Optics; © 2009 Metamorphose-VI; Centre for Nanostructured Media, IRCEP, The Queen's University of Belfast, Belfast, BT7 1NN, United Kingdom; 328-330.

Robbie et al.; Thin films with nanometer-scale pillar microstructure; J. Mater. Res., vol. 14, No. 7, Jul 1999 © 1999 Materials Research Society; 3158-3163.

Yang et al.; Nanomachining by Colloidal Lithography; small 2006, 2, No. 4, 458-475.

Zhang et al.; Colloidal Lithography—The Art of Nanochemical Patterning; Chem. Asian J. 2009, 4, 236-245; DOI: 10.1002/asia.200800298.

* cited by examiner

SURFACE ENHANCED RAMAN SCATTERING (SERS) APPARATUS, METHODS AND APPLICATIONS

CROSS REFERENCE TO RELATED APPLICATION

This application is related to, and derives priority from, U.S. Provisional Patent Application Ser. No. 61/528,820 filed on 30 Aug. 2011 and titled Surface Enhanced Raman Scattering (SERS)-Based Nanostructured Apparatus, Method and Applications, the subject matter of which is fully incorporated herein by reference.

STATEMENT OF GOVERNMENT INTEREST

The research underlying the embodiments described herein and the invention claimed herein was funded by the United States National Institutes of Health under grant number R21EB007031 and the United States National Science Foundation under grant number ECS-0876771. The United States Government has certain rights in the invention.

Embodiments of the invention generally relate to the field of molecular spectroscopy and, particularly to apparatus and fabrication and analysis methods associated with surface-enhanced Raman scattering (SERS). More particularly, embodiments relate to particular nanostructured substrates, their fabrication, and their use in enhanced molecular spectroscopy analysis.

The high sensitivity and potential for label-free analysis associated with surface enhanced Raman scattering (SERS) spectroscopy has made it an attractive analytical technique for applications ranging from DNA sequencing to pathogen identification. However, acquisition of reproducible SERS spectroscopic analyses over large areas often requires nanostructured substrate arrays with precisely controlled shapes and sizes. Uniformity of the nanostructured substrates over large scales is important, since Raman signal intensity is often extremely sensitive to the size, shape, and morphology of the nanostructures on a substrate.

Thus, given the desirability of SERS analysis in various fields, nanostructured substrates and their methods for manufacture, with enhanced nanostructure uniformity that provides enhanced surface enhanced Raman scattering properties, are also desirable.

Non-limiting embodiments of the invention include various SERS enhanced nanostructured substrates each having different nanostructures created by adjusting fabrication parameters, a method for fabricating the SERS enhanced nanostructured substrate, and a SERS detection method that uses the SERS enhanced nanostructured substrate.

Associated with the foregoing SERS enhanced nanostructured substrate and related methods are novel and reproducible nanostructures. Moreover, the embodiments provide a high throughput method for creating uniform, large area, and flexible SERS-active substrates. Flexible and large area SERS substrates are useful because they can be more easily incorporated into irregularly shaped surfaces such as clothing, and have greater spatial area for multiplexing. Within the context of the embodiments, a method in accordance with the embodiments is referred to as 'shadow mask assisted evaporation' (SMAE).

An embodiment of the invention is a composite structure. In an exemplary, non-limiting aspect, the composite structure includes a substrate and an at least 3×3 array of nanostructures disposed on the substrate, wherein each nanostructure has an elongate shape and a distal end in the form of an open, pointed tip. According to various non-limiting aspects, the composite structure may be characterized by one or more of the following:

wherein the substrate is a flexible substrate;
wherein the substrate is an elastomeric material;
wherein the substrate is PDMS;
wherein the substrate is characterized by a spatial area that enables multiplexing (i.e., as used herein, multiplexing means the ability to perform more than one reaction in parallel; e.g., on the embodied substrate one reaction could occur on the left side and a different one on the right side. Because the area is relatively large compared to the detection areas, it may be possible to create a large number of detection sites on a single surface);
wherein the substrate is a dielectric material and the nanostructures comprise a conductor material;
wherein the nanostructures comprise at least one of silver, gold, copper, aluminum, and a combination thereof;
wherein each nanostructure is selected from the group consisting of a non-enclosed-nano-pillar, a semi-enclosed nano-nib, a semi-enclosed nano-ellipsoidal cylinder, and a non-enclosed nano-triangular tip;
wherein each non-enclosed-nano-pillar has an elongate dimension from about 390 nm to about 500 nm and a diametrical dimension from about 150 nm to about 200 nm;
wherein each semi-enclosed nano-nib has an elongate dimension from about 445 nm to about 465 nm and a diametrical dimension from about 145 nm to about 200 nm;
wherein each semi-enclosed nano-ellipsoidal cylinder has an elongate dimension from about 285 nm to about 360 nm and a diametrical dimension from about 140 nm to about 190 nm;
wherein each non-enclosed nano-triangular tip has an elongate dimension from about 195 nm to about 250 nm and a diametrical dimension from about 145 nm to about 205 nm;
wherein the nanostructure array has an inducible variable spacing;
further comprising a plurality of functionalized nanoparticles each one of which is attached to a surface of a respective nanostructure, wherein each nanoparticle comprises a material characterized by an atomic weight that is greater than an atomic weight of the nanostructure to which it is attached;
wherein the functionalized nanoparticles comprise gold spheres having a concentration of a TAMRA-labeled target probe.

An embodiment of the invention is a method of making a composite structure. In an exemplary, non-limiting aspect, a method for making a composite structure having an at least 3×3 array of nanostructures includes the steps of providing a three-dimensional, periodically-arrayed nano-porous template; disposing the template in the path of a vaporized metal in an E-beam evaporator system at a fixed angle, $\alpha$, where $\alpha$ is equal to or less than +60 degrees relative to the vaporized metal evaporation path axis; depositing a desired thickness of the metal on a top surface and at least a portion of an interior surface of each nanopore of the template while controlling a rotation of the template, thereby forming a deposited metal nanoarray structure, wherein each of the arrayed nanostructures has a pointed distal tip; eliminating the template leaving only the remaining deposited metal nanoarray structure; and attaching the remaining deposited metal nanoarray structure to a support substrate. According to various non-limiting aspects, the method may be characterized by one or more of the following steps and/or features:

further comprising attaching each one of a plurality of functionalized nanoparticles to a surface of a respective nanostructure, wherein each nanoparticle comprises a material characterized by an atomic weight that is greater than an atomic weight of the nanostructure to which it is attached;

wherein the attaching step further comprises attaching the remaining deposited metal nanoarray structure to a flexible support substrate;

further comprising attaching the remaining deposited metal nanoarray structure to an elastomeric substrate;

further comprising attaching the remaining deposited metal nanoarray structure to a PDMS substrate;

further comprising disposing the template at the fixed angle $\alpha$, where $\alpha$ is less than or greater than 0 degrees; and depositing the desired thickness of the metal in a single step, wherein the remaining deposited metal nanoarray structure is a periodic array of non-enclosed-nano-pillars;

wherein $\alpha$=45 degrees, further comprising deposing silver at a deposition rate of 0.8 angstroms per second;

further comprising depositing a first desired thickness of metal at a first angle $\alpha$ with no template rotation; and depositing a second desired thickness of metal at the first angle $\alpha$ while substantially fully rotating the template, wherein the remaining deposited metal nanoarray structure is a periodic array of semi-enclosed nano-nibs;

wherein $\alpha$=45 degrees, further comprising rotating the template at about 35 rpm;

further comprising depositing a first desired thickness of metal at a first angle $\alpha$ while fully rotating the template; and depositing a second desired thickness of metal at the first angle $\alpha$ with no template rotation, wherein the remaining deposited metal nanoarray structure is a periodic array of semi-enclosed nano-ellipsoidal cylinders;

wherein $\alpha$=45 degrees, further comprising rotating the template at about 35 rpm;

further comprising depositing a first desired thickness of metal at a first angle, $\alpha$, with no template rotation; and depositing a second desired thickness of metal at a second angle, $-\alpha$, with no template rotation, wherein the remaining deposited metal nanoarray structure is a periodic array of non-enclosed nano-triangular tips' wherein $\alpha$=45 degrees;

further comprising tuning an optical response of the remaining deposited metal nanoarray structure.

further comprising applying a mechanical stress to the remaining deposited metal nanoarray structure.

The objects, features and advantages of the embodiments are understood within the context of the Detailed Description of the Embodiments, as set forth below. The detailed description of non-limiting, exemplary embodiments, which follows below, will be understood within the context of the accompanying drawings, which form a material part of this disclosure, wherein:

FIG. 1b(1-4) show a series of scanning electron microscopy images of silver 'nano-pillars' located and formed upon a substrate to provide a SERS substrate fabricated using a SMAE method, in accordance with an aspect of the invention;

FIGS. 2(a-d) show a series of scanning electron microscopy images illustrating different effects of incidence angle upon substrate morphology when forming a SERS substrate using a SMAE method, according to an illustrative aspect of the invention;

FIGS. 3(a-d) show a series of diagrams illustrating an influence of deposition conditions upon deposited structure, to provide four different deposited structures when fabricating a SERS substrate using a SMAE method, according to an illustrative aspect of the invention;

FIGS. 4(a-d) show a series of scanning electron microscopy images illustrating the four different deposited structures in accordance with FIG. 3, but at greater magnification;

FIG. 5 is a graph that shows a series of SERS spectra of immobilized TAMARA labeled DENV-2a virus with respect to the four SERS substrates shown in FIG. 3; and FIGS. 6(*a-c*) show various diagrams illustrating the integration of gold nanoparticles with SERS substrates for an enhanced SERS response, according to an illustrative aspect of the invention.

The disclosed embodiments and aspects provide an enhanced SERS substrate, a method for fabricating the enhanced SERS substrate, and a Raman spectroscopy method that uses the enhanced SERS substrate. In particular, the method for fabricating the enhanced SERS substrate uses a SMAE method that utilizes a shadow mask for fabricating reproducible SERS substrates.

An exemplary embodiment of the invention is illustrated in FIG. 1*a*. FIG. 1*a* shows a schematic of the SMAE process. Briefly, gold (Au) is SMAE-deposited on an anodized aluminum oxide (AAO) nanoporous template 101 at an angle, α, such that at least a portion of the inner walls and the top surface of the nanoporous template will be coated. Following evaporation, the AAO nanoporous template is dissolved in a NaOH solution and the surviving metallic nanostructured film 105 is allowed to settle onto the top of a poly(dimethylsiloxane) (PDMS) substrate 102 (further fabrication details are described below). Large (e.g., 27 to 47 mm and, theoretically, larger; see, e.g., (http://www.whatman.com/PROD/AnoporeInorganicMembranes.aspx) nanostructure arrays may be constructed using the embodied technique, limited only by the size of the template. This particular SMAE methodology has numerous advantages over competing art including greater simplicity in fabrication, lower cost, substrate flexibility, and relatively larger fabricated area.

Other metals in addition to gold such as silver, copper, aluminum, and combinations thereof may alternatively be deposited on an AAO or other suitable nanoporous template.

FIG. 1*b*(1,2,3,4) show a series of SEM images of Ag "nano-pillar" structures (305, FIG. 3*a*) obtained using a 45 degree incident deposition angle (α), and evaporation rates of: (1) 0.8 angstroms per second; and (2) 1.2 angstroms per second. The tips of the 'nano-pillar' structures shown in FIG. 1*b*(1) (445+/−55 nm; single structure height+/−standard deviation) are much sharper than those shown in FIG. 1*b*(2) (340+/−45 nm), suggesting that higher evaporation rates yield coarser structures.

As shown in FIG. 1*b*(3) and FIG. 1*b*(4), the placement of the nanostructured film on a PDMS support enables these substrate-supported nanoarrays to be robust and highly flexible. In addition to the advantages described above, this flexibility may allow the spacing of the nano-pillars to be modified by mechanical stress, which could be useful for tuning the optical response.

Nano-pillars were also performed for a equal to 30 degrees and 60 degrees, the results of which can be seen in FIGS. 2(*a,b*) and 2(*c,d*), respectively. The 30 degree angle of evaporation yielded sharper nanostructures than the 60 degree deposition. However, during the dissolution of the AAO membrane the relatively tall and weak pillars tended to collapse (see FIG. 2a and FIG. 2b). For the 60 degree incident angle of evaporation, shadowing resulted in shorter and less sharp nano-pillars (see FIG. 2c and FIG. 2d) than were observed for the 45 degree incident angle of evaporation case. Stronger fields are normally achieved from sharper morphologies. Based on the above results, evaporation conditions at an incident angle of 45 degrees and a deposition rate of 0.8 angstroms per second were chosen as the optimal conditions and used for the remainder of the disclosed exemplary embodiments.

Figure 1:
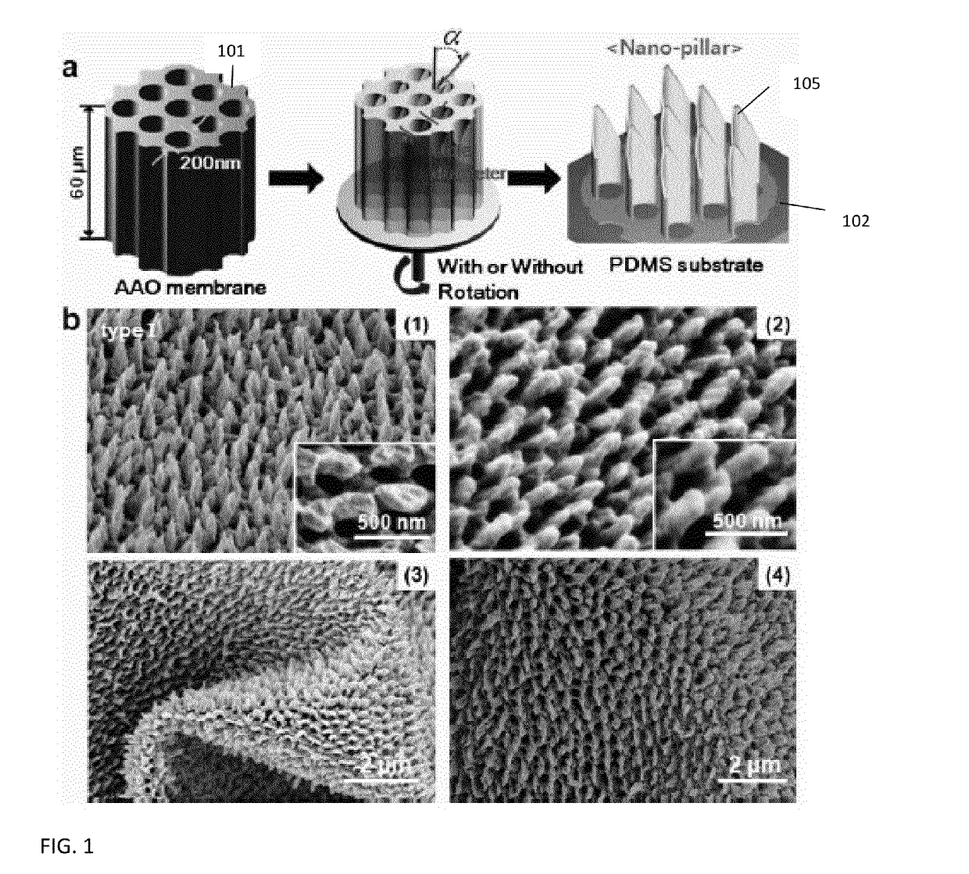
FIG. 1a shows a series of schematic diagrams illustrating progressive process stages in fabricating a SERS substrate in accordance with a SMAE method, according to an embodiment of the invention.
Figure 2:
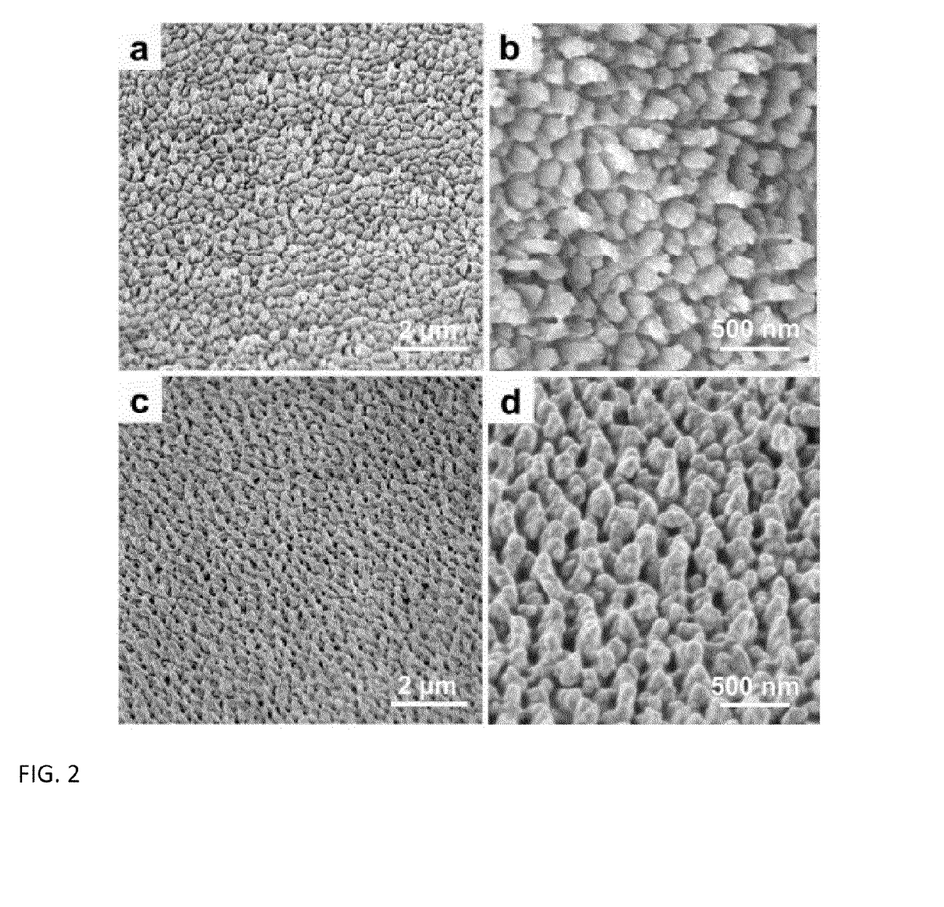
Figure 3:
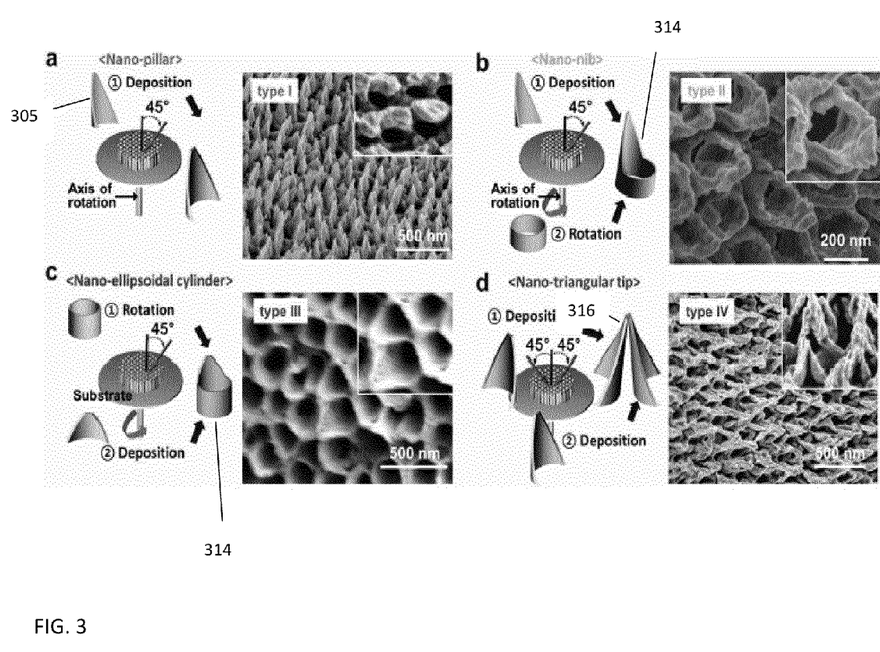
Figure 4:
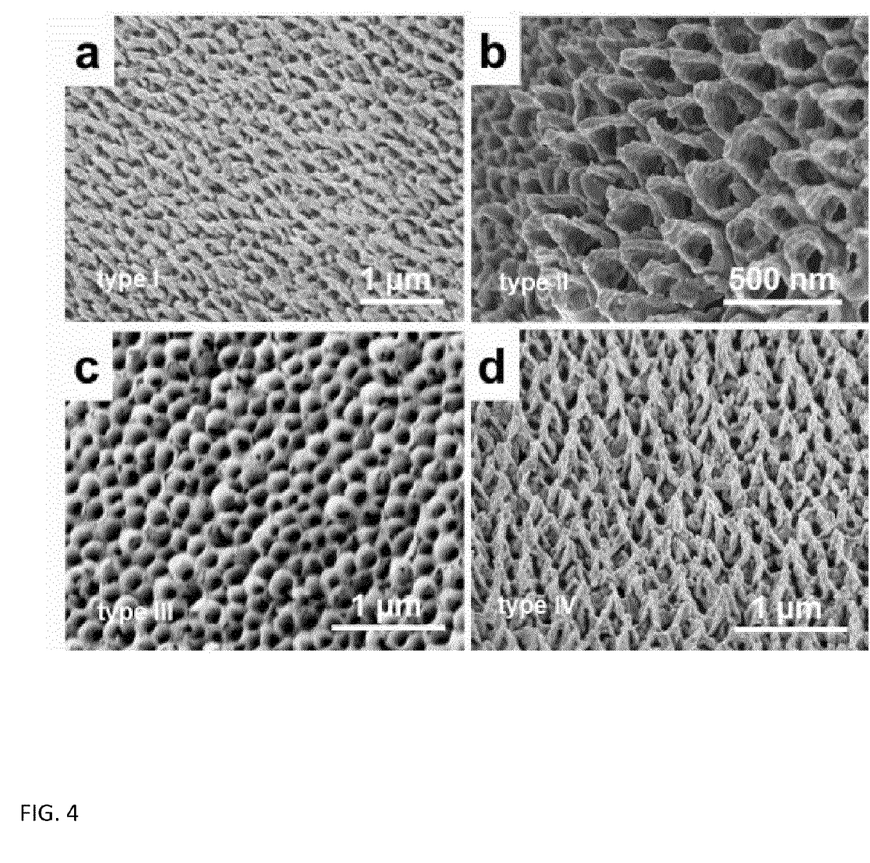

To further explore the methodology used to create the nano-pillars 305 as illustrated in FIG. 3a, three additional types of nanostructure arrays were fabricated using the embodied methods. FIG. 3b illustrates "nano-nib" shaped (type II) structures 312 obtained through a double evaporation process. To fabricate this structure, 100 nm of silver was first deposited at a 45 degree incident angle. An additional 100 nm of silver was then deposited with a equal to 45 degrees and a substrate rotation speed of 35 rpm. We observed arrays of structures 405+/−57 nm in height with 173+/−25 nm hole diameters (as defined in FIG. 1a). In another approach, 'nano-ellipsoidal cylinder' (type III) structures 314 as illustrated in FIG. 3c were fabricated using the same conditions except that the substrate 101 was rotated during the initial metal deposition and then not rotated for the second silver evaporation step. Measured height and hole diameters, respectively, were 320+/−35 nm and 165+/−21 nm. A fourth type of nanostructure was obtained by depositing silver twice with a equal to 45 degrees and 135 degrees. The resulting "nano-triangular tip" structures (type IV) 316 shown in FIG. 3d had a height of 220+/−24 nm and a hole diameter of 175+/−27 nm. Table 1 summarizes the fabrication conditions and specifications for the exemplary nanostructures disclosed herein. Although only a small portion of the entire substrate can be imaged (wider view SEM images are shown in FIG. 4), all nanostructure arrays exhibited high periodicity and uniformity. Various hole sizes can be obtained using different AAO templates; e.g., membranes with nanopores ranging from 20 to 200 nm in diameter are commercially available.

TABLE 1

| Parameters/type | Nano-pillar (type I) | Nano-nib (type II) | Nano-ellipsoidal cylinder (type III) | Nano-triangular tip (type IV) |
| --- | --- | --- | --- | --- |
| Height/nm | 445 ± 55 | 405 ± 57 | 320 ± 35 | 220 ± 24 |
| Hole diameter/nm | 178 ± 20 | 173 ± 25 | 165 ± 21 | 175 ± 27 |
| Deposition thickness/nm | 200 | 100/100 | 100/100 | 100/100 |
| Angle/degree | 45° | 45°/0 | 0°/45° | 45°/135° |
| Rotation | No | No/yes | Yes/no | No/no |
| Relative sensitivity (±SD) | 1.94 ± 0.12 | 1.82 ± 0.22 | 1 | 2.4 ± 0.35 |

Raman Characterization

Figure 5:
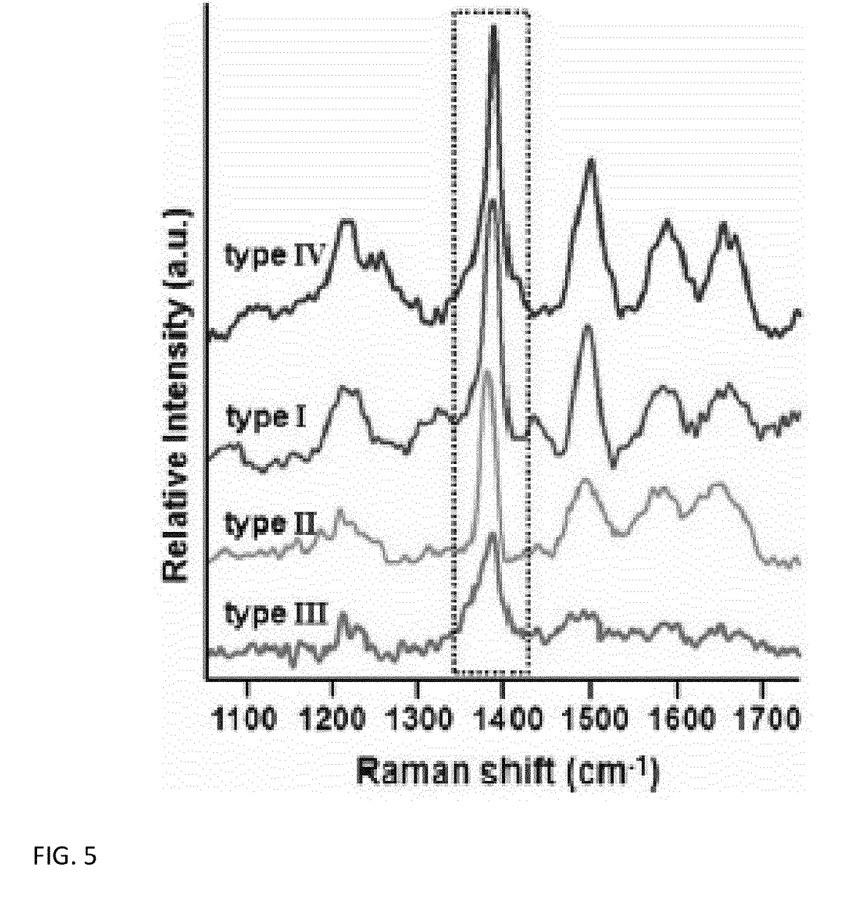

Raman signatures were obtained to characterize the relative sensitivity of each nanostructure array in accordance with the foregoing embodiments. As described in greater detail below, TAMRA-labeled nucleic acid sequences analogous to Dengue virus serotype 2 (DENV-2a) were used as detection targets. To facilitate biocompatibility, prior to conducting the experiments each silver nanostructure e.g., nano-pillar 305 (as described above), was coated with 5 nm of gold. FIG. 5 is a graph that shows the SERS spectra obtained from the four different SERS-active substrates (y-axis: relative intensity; x-axis: Raman shift ($cm^{-1}$)). In all cases, a solution containing 300 nM of the target DNA was pipetted onto the surface. Negative controls were not conducted here as the goal of this experiment was to measure the relative sensitivity of the surfaces using a common sample rather than conduct a formal detection reaction. As expected, characteristic Raman peaks for the TAMRA-labeled DNA were found at 1640, 1573, 1482, 1385, and 1217 $cm^{-1}$. As illustrated in the dashed box in FIG. 5, the difference in Raman intensity at 1385 $cm^{-1}$ was used for relative sensitivity evaluation. The nano-triangular tip (type IV) and nano-ellipsoidal cylinder (type III) are observed to be the most and least sensitive arrays, respectively. Comparing the relative sensitivity of the other structures to the nano-ellipsoidal cylinder yielded enhancements of: 1.82+/−0.22 for the nano-nib (average+/− standard deviation), 1.94+/−0.12 for the nano-pillar, and 2.4+/−0.35 for the nano-triangular tip structure. Although the nano-triangular tip arrays (type IV) had the greatest enhancement owing to their sharper tip morphology, the nano-pillar arrays (type I) showed the most reproducible SERS signals (smallest standard deviation). A reason for this greater reproducibility may be because the type I structures are made using a single step fabrication process (as opposed to the type IV which uses a double step process).

Integration of Nanostructured Substrates with Au Nanoparticles

Figure 6:
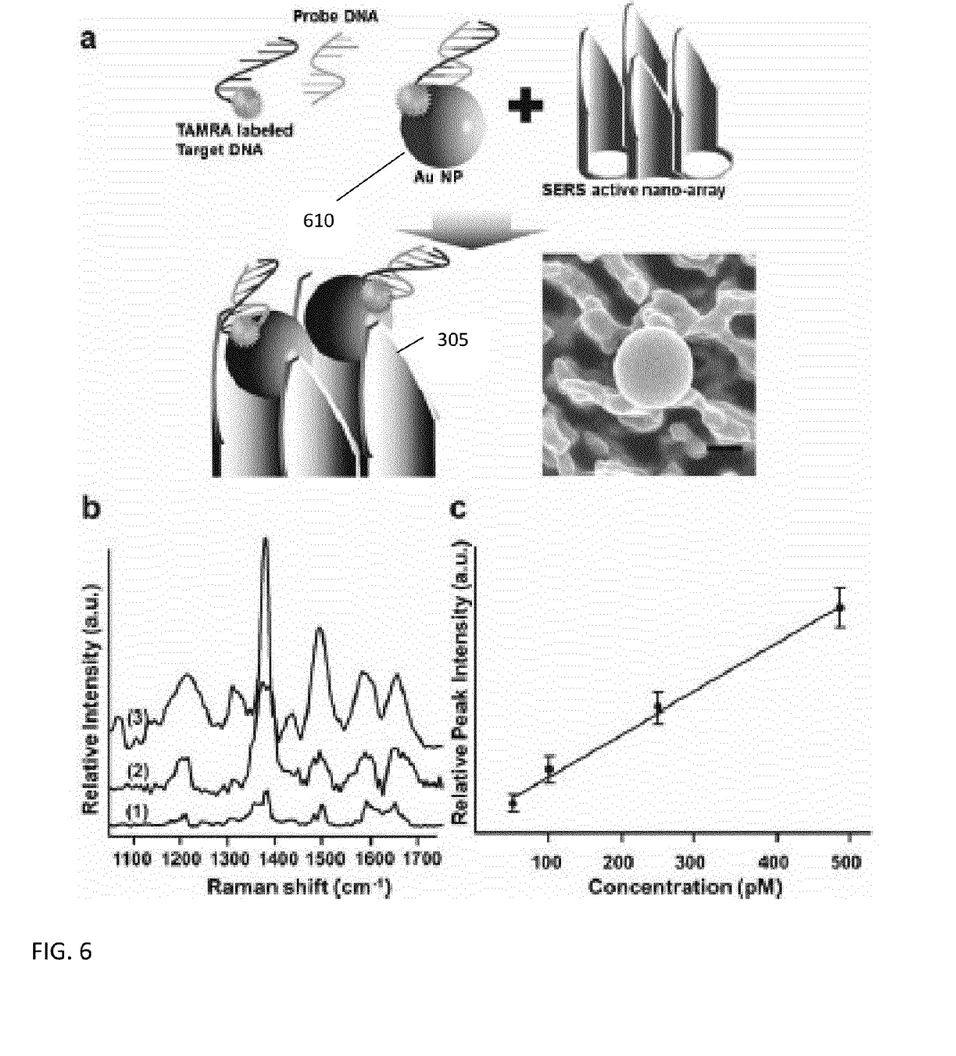

The Raman signals from the embodied nanostructured surfaces can be further enhanced by integrating them with Au nanoparticles. This may be embodied with the nano-pillar array (type I) substrate as it exhibited the greatest reproducibility. FIG. 6a and FIG. 6b schematically show how the nanoparticles 610 settle into the nanostructures 305. The close interaction between the pillars and the nanoparticles causes a coupling of the plasmonic resonances leading to a localized hot spot as has been previously suggested. As shown in FIG. 6a and FIG. 6b, TAMRA-labeled DENV-2a was attached to the Au nanospheres, not to the Ag SERS-active substrate. FIG. 6b shows the resulting SERS spectra from the: (1) 200 nm Au nanoparticles after settling on the surface; (2) Ag nano-pillar substrate without nanoparticles (similar to the type I experiment in FIG. 5 for comparison); and (3) 200 nm Au nanoparticles embedded in the nano-pillar arrays. As can be seen, integrating the gold nano-particles with the nano-pillar array yielded a response approximately 50 times higher than the nanoparticle themselves at 1385 $cm^{-1}$. Experiments were also conducted using different concentrations of TAMRA-labeled target probes (50 μM, 100 μM, 250 μM, and 500 μM). As can be seen in FIG. 6c, the intensity of the peak at 1385 $cm^{-1}$ increased linearly with the concentration over this range, suggesting that the linear trend in the small concentration range can be used for quantitative analysis as well.

Materials and Methods

AAO membranes (Whatman Anodisc, 60 mm thick, 200 nm diameter pores) were fixed onto a silicon wafer substrate using Kapton tape. The chuck angle was altered from 30 degrees to 60 degrees. Metals (gold and silver) were deposited using a CVC SC4500 apparatus (CVC Inc., NY). After the metal deposition, the membranes were detached from the silicon substrate and were immersed in a 3.0 M NaOH solution for 10 min to fully dissolve the AAO sacrificial templates. Following this, the metal nanostructure films were dipped in 30 mM 3-mercaptopropyl-trimethoxysilane (MPTMS) solution for 2 hours, which assists the metal film in adhering to the PDMS. After 2 hours the MPTMS solution was replaced with deionized (DI) water and a piece of polymerized PDMS was introduced. The DI water was then gently extracted using a micropipette and the thin metal film was allowed to settle onto the top of the PDMS. The final device was dried in an oven at 80° C. for 1 hour.

Raman Measurements

Raman signatures were measured using a Renishaw in Via Raman spectrometer (Renishaw, UK) coupled to a Leica microscope with a 785 nm laser (spectral resolution of approximately 0.1 $cm^{-1}$). A 50× (NA=0.75) objective lens was used to focus the laser beam onto the sample surface and the scattered signal was collected by a Peltier cooled CCD detector. Wave-numbers ranging from 1000 $cm^{-1}$ to 1800 $cm^{-1}$ were examined with respect to the embodiments. Raman signals were obtained from at least three different spots on each nanostructured surface.

Sample Preparation

Dengue virus serotype 2 (DENV-2) was chosen as the target analyte and purchased from Operon Biotechnologies (Huntsville, Ala.). The target probe of DENV-2a was modified with TAMRA dye and a thiol-modifier containing C3 S—S functionality. The titrations of TAMRA-labeled target probes were prepared by diluting the proper amount of DNA in a 10 mM PBS buffer solution (0.6 MNaCl, pH 7.4). The 200 nm diameter gold nanoparticles were purchased from Nanocs (New York, N.Y.).

We have demonstrated a new high throughput technique for creating large area, flexible SERS-active substrates by shadow mask assisted evaporation (SMAE). Controlling the evaporation parameters (incident angle, rotation, and deposition rate), enabled numerous, different topographies to be obtained. We characterized each of these topographies demonstrating that a nano-triangular tip has the largest Raman enhancement and a nano-pillar tip has the highest repeatability. Integration of these substrates with gold nanoparticles yielded enhanced plasmonic hotspots, resulting in a 50-fold improvement over just the nanoparticles themselves.

All references, including publications, patent applications, and patents cited herein are hereby incorporated by reference in their entireties to the extent allowed, and as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A composite structure comprising a substrate; and an at least 3×3 array of nanostructures disposed on the substrate, wherein each nanostructure has an elongate shape and a distal end in the form of an open, pointed tip and a plurality of functionalized nanoparticles each one of which is attached to a surface of a respective nanostructure, wherein each nanoparticle comprises a material characterized by an atomic weight that is greater than an atomic weight of the nanostructure to which it is attached.

2. The structure of claim 1, wherein the substrate is a flexible substrate.

3. The structure of claim 2, wherein the substrate is an elastomeric material.

4. The structure of claim 3, wherein the substrate is polydimethylsiloxane (PDMS).

5. The structure of claim 1, wherein the substrate is a dielectric material and the nanostructures comprise a conductor material.

6. The structure of claim 1, wherein the nanostructures comprise at least one of silver, gold, copper, aluminum, and a combination thereof.

7. The structure of claim 1, wherein each nanostructure is selected from the group consisting of a non-enclosed-nano-pillar, a semi-enclosed nano-nib, a semi-enclosed nano-ellipsoidal cylinder, and a non-enclosed nano-triangular tip.

8. The structure of claim 1, wherein the nanostructure array has an inducible variable spacing.

9. The structure of claim 7, wherein each non-enclosed-nano-pillar has an elongate dimension from about 390 nm to about 500 nm and a diametrical dimension from about 150 nm to about 200 nm.

10. The structure of claim 7, wherein each semi-enclosed nano-nib has an elongate dimension from about 445 nm to about 465 nm and a diametrical dimension from about 145 nm to about 200 nm.

11. The structure of claim 7, wherein each semi-enclosed nano-ellipsoidal cylinder has an elongate dimension from about 285 nm to about 360 nm and a diametrical dimension from about 140 nm to about 190 nm.

12. The structure of claim 7, wherein each non-enclosed nano-triangular tip has an elongate dimension from about 195 nm to about 250 nm and a diametrical dimension from about 145 nm to about 205 nm.

13. The structure of claim 1, wherein the functionalized nanoparticles comprise gold spheres having a concentration of a TAMRA-labeled target probe.

14. A method of making an at least 3×3 array of nanostructures, comprising:
   providing a three-dimensional, periodically-arrayed nanoporous template;
   disposing the template in the path of a vaporized metal in an E-beam evaporator system at a fixed angle, α, where α is equal to or less than +60 degrees relative to the vaporized metal evaporation path axis;

depositing a desired thickness of the metal on a top surface and at least a portion of an interior surface of each nanopore of the template while controlling a rotation of the template, thereby forming a deposited metal nanoarray structure, wherein each of the arrayed nanostructures has a pointed distal tip;

eliminating the template leaving only the remaining deposited metal nanoarray structure; and attaching the remaining deposited metal nanoarray structure to a support substrate.

15. The method of claim 14, further comprising attaching each one of a plurality of functionalized nanoparticles to a surface of a respective nanostructure, wherein each nanoparticle comprises a material characterized by an atomic weight that is greater than an atomic weight of the nanostructure to which it is attached.

16. The method of claim 14, wherein the attaching step further comprises attaching the remaining deposited metal nanoarray structure to a flexible support substrate.

17. The method of claim 16, further comprising attaching the remaining deposited metal nanoarray structure to an elastomeric substrate.

18. The method of claim 17, further comprising attaching the remaining deposited metal nanoarray structure to a polydimethylsiloxane (PDMS) substrate.

19. The method of claim 14, further comprising:
disposing the template at the fixed angle $\alpha$, where $\alpha$ is less than or greater than 0 degrees; and
depositing the desired thickness of the metal in a single step,
wherein the remaining deposited metal nanoarray structure is a periodic array of non-enclosed-nano-pillars.

20. The method of claim 14, wherein $\alpha$=45 degrees, further comprising deposing silver at a deposition rate of 0.8 angstroms per second.

21. The method of claim 14, further comprising:
depositing a first thickness of metal at a first angle $\alpha$ with no template rotation; and
depositing a second thickness of metal at the first angle $\alpha$ while substantially fully rotating the template,
wherein the remaining deposited metal nanoarray structure is a periodic array of semi-enclosed nano-nibs.

22. The method of claim 21, wherein $\alpha$=45 degrees, further comprising rotating the template at about 35 rpm.

23. The method of claim 14, further comprising:
depositing a first thickness of metal at a first angle $\alpha$ while fully rotating the template; and
depositing a second thickness of metal at the first angle $\alpha$ with no template rotation,
wherein the remaining deposited metal nanoarray structure is a periodic array of semi-enclosed nano-ellipsoidal cylinders.

24. The method of claim 23, wherein $\alpha$=45 degrees, further comprising rotating the template at about 35 rpm.

25. The method of claim 14, further comprising:
depositing a first thickness of metal at a first angle, $\alpha$, with no template rotation; and depositing a second thickness of metal at a second angle, $-\alpha$, with no template rotation,
wherein the remaining deposited metal nanoarray structure is a periodic array of non-enclosed nano-triangular tips.

26. The method of claim 25, wherein $\alpha$=45 degrees.

27. The method of claim 14, further comprising tuning an optical response of the remaining deposited metal nanoarray structure.

28. The method of claim 27, further comprising applying a mechanical stress to the remaining deposited metal nanoarray structure.

* * * * *